United States Patent [19]
Raffel

[11] 3,934,283
[45] Jan. 27, 1976

[54] BED FRAME WITH READILY CONNECTABLE VIBRATOR MOTORS

[76] Inventor: Marvin J. Raffel, 9094 N. 75th St., Apt. 1B, Milwaukee, Wis. 53223

[22] Filed: June 17, 1974

[21] Appl. No.: 479,703

[52] U.S. Cl............. 5/109; 24/262 R; 248/18
[51] Int. Cl.²........................... A61H 1/000
[58] Field of Search ............... 5/108, 109; 128/33; 298/18, 20; 24/248 SA, 242 CC, 262 R, 263 A, 263 LS

[56] References Cited
UNITED STATES PATENTS

| | | | |
|---|---|---|---|
| 2,519,107 | 8/1950 | Brown | 24/262 R |
| 2,916,745 | 12/1959 | Lesk et al. | 5/109 |
| 3,032,849 | 5/1962 | Cohen et al. | 24/262 R |
| 3,035,572 | 5/1972 | Houghtaling | 128/33 |
| 3,048,167 | 8/1962 | Kamp | 128/33 |
| 3,154,704 | 10/1964 | Shaffer | 248/18 |
| 3,653,375 | 4/1972 | Raffel | 128/33 |

Primary Examiner—Casmir A. Nunberg
Attorney, Agent, or Firm—Arthur L. Morsell, Jr.

[57] ABSTRACT

Two vibrator motors are removably attached to opposite rail portions of a bed frame or bed rail by clamp arms which project laterally from one side of each motor housing to hold the motor in a position which is offset from the bed springs. The rail-engaging ends of the clamp arms are covered by resilient caps which grip the rail to prevent the clamp arms from being shaken loose by the vibrator motor. The other ends of the clamp arms of each motor are connected to an elongated bracket which is cast as an integral part of the motor housing, and one of the clamp arms is adjustable relative to the other clamp arm.

2 Claims, 5 Drawing Figures

U.S. Patent   Jan. 27, 1976   3,934,283
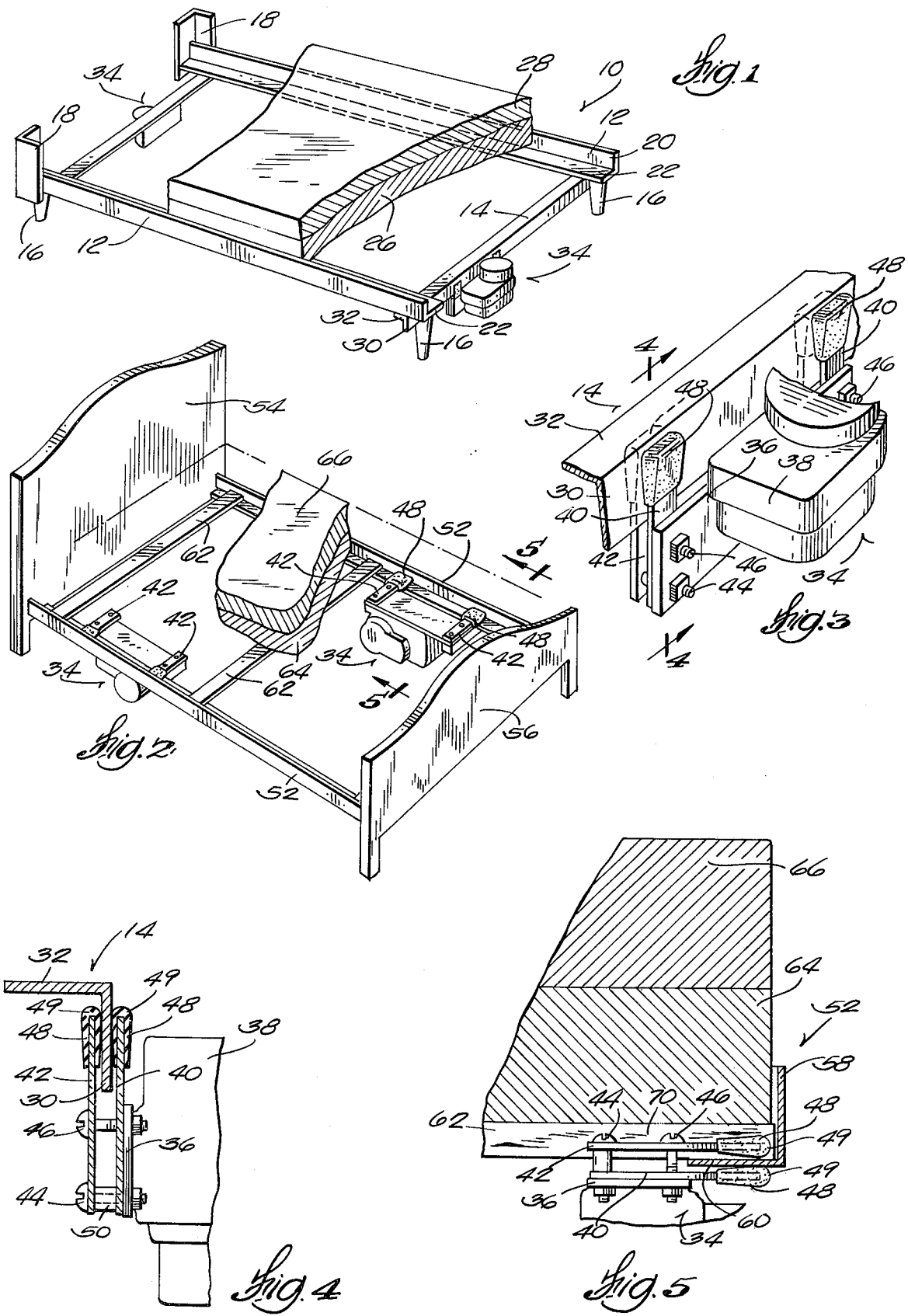

BED FRAME WITH READILY CONNECTABLE VIBRATOR MOTORS

BACKGROUND OF THE INVENTION

This invention relates to means for vibrating a bed to massage the occupant or occupants thereof, thereby relaxing their muscles and inducing sleep. The invention provides improvements in the positioning of the vibrator motors and in the means by which the vibrator motors are readily attached to a standard bed frame without altering the same or drilling holes. Heretofore it has been customary to secure a vibrator motor to the wooden frame which forms part of a box spring. This, however, is very undesirable. With the present invention a change to a different box spring may be readily made without disturbing the vibrator.

SUMMARY OF THE INVENTION

In accordance with this invention, one or more vibrator motors are attached to rail portions of a standard bed frame in positions which are offset from the bed springs. Each vibrator motor is readily removably clamped to a rail portion of the bed frame by clamp arms which project laterally from one side of the motor housing and securely grip the rail. Thus it is unnecessary to drill holes in the rails or box spring frame or otherwise alter the bed frame or box spring frame to attach the vibrator motors thereto. The rail-engaging ends of the clamp arms are preferably covered by resilient caps. The clamp arms are arranged in spaced pairs at the ends of an elongated mounting bracket attached to the vibrator motor housing. One arm of each pair of clamp arms is adjustable toward and away from the other to provide a proper setting so that a rail will be tightly gripped therebetween when the clamp arms are manually pushed into assembled position.

A general object of the invention is to provide an arrangement which makes it possible to easily install the vibrator motors on standard bed frames or bed rails without alteration or drilling, and to easily remove the vibrator motors therefrom.

A further object is to provide an arrangement which provides no interference with the placement or removal of the box spring and mattress.

DESCRIPTION OF THE DRAWINGS

FIG. 1 is a perspective view of one type of bed frame having vibrator motors clamped to opposite end rails thereof;

FIG. 2 is a perspective view of another type of bed having vibrator motors clamped to opposite side rails thereof;

FIG. 3 is an enlarged perspective view of one of the vibrator motors shown in FIG. 1 showing the means for clamping the motor to the end rail portion of the bed frame;

FIG. 4 is a cross-sectional view taken on the line 4—4 of FIG. 3; and

FIG. 5 is a cross-sectional view taken on the line 5—5 of FIG. 2.

DESCRIPTION OF THE PREFERRED EMBODIMENTS

FIG. 1 shows one type of standard bed frame 10 which includes two opposed steel side rails 12 and two opposed steel end rails 14 which are arranged in a rectangular pattern and are riveted or otherwise secured together at their corners. Frame 10 is supported by four feet 16 which are each welded to a corresponding corner of frame 10 or are attached thereto by bolts. Two corner brackets 18 are welded to the head end of side rails 12 as is customary.

The side rails 12 are L-shaped in cross-section with an upstanding flange portion 20 and an inwardly-directed flange portion 22. The flange portions 22 support a set of springs 26 and a mattress 28. The end rails 14 are also L-shaped in cross-section and have a downwardly-directed flange portion 30 and an inwardly-directed flange portion 32. Two vibrator motors 34 are attached to the flange portion 30 of opposite end rails 14 to produce interfering vibratory waves in accordance with the principles described in my U.S. Pat. No. 3,653,375, which discloses a method of controlling the differential speed of two vibrator motors mounted on opposite portions of a closed rigid frame to set up differential vibrations in the frame and the structure supported thereby. It should be understood, however, that this invention is concerned with the positioning of the vibrator motors relative to the bed structure and with the means for attaching the vibrator motors to the bed frame. Accordingly, it should be understood that this invention is also applicable to cases where only a single vibrator motor is attached to the bed frame 10.

The means for attaching vibrator motors 34 to end rails 14 is shown most clearly in FIGS. 3 and 4. The vibrator motors 34 contain an eccentrically-mounted weight on their drive shaft so as to produce a pronounced mechanical vibration as the drive shaft rotates. This vibration is mechanically coupled to end rails 14 by the attachment means therefor, and the attachment means must, therefore, be sturdy enough to withstand this vibration and must be clamped tightly enough to end rails 14 to preclude being shaken loose by the vibration. One important feature of this invention is that it provides attachment means which can be quickly installed on a standard bed frame and which will hold in place in spite of the vibration without requiring any alteration or the drilling of holes in rails 14. Another important feature of this invention is that the attachment means is arranged to hold the vibrator motor 34 in a position which is offset from the springs 26 regardless of whether the vibrator motors 34 are attached to end rails 14 or to side rails 12. These two features allow the vibrator motors 34 to be attached to standard bed frames without requiring any modification thereof. Additional features, described below, enable the vibrator motors 34 to be quickly and easily attached in place or removed.

Referring to FIGS. 3 and 4, the attachment means for vibrator motor 34 includes an elongated bracket 36 which is rigidly attached to one side of motor housing 38, preferably by being cast as an integral part of the adjacent portion of housing 38. The vibrator motor 34 is entirely located on one side of bracket 36 to permit motor 34 to clear the rail to which it is attached, and to be offset from springs 26 in the case where motor 34 is attached to side rails 12. Two pairs of clamp arms including inner clamp arms 40 and outer clamp arms 42 are bolted to opposite ends of bracket 36 and project laterally therefrom. Bracket 36 is elongated at both ends beyond motor housing 38 for ease of access to the attachment points of clamp arms 40 and 42, which are bolted to bracket 36 by end bolts 44 and by intermediate bolts 46. Bolts 44 and 46 pass through corresponding bores in clamp arms 40, 42 and in the ends of bracket 36.

Resilient end caps 48, which may be made of rubber or a suitable plastic material, are preferably fitted on the ends of clamp arms 40, 42 to tightly grip the flange portions 30 of end rail 14. End caps 48 preferably flare outwardly to provide a relatively enlarged outer end (FIG. 4). Spacer sleeves 50 on end bolts 44 are provided between the inner ends of clamp arms 40, 42. Spacer sleeves 50 are of such length as to space end caps 48 apart by a distance approximately equal to the thickness of the metal of flange portion 30 of end rail 14. Intermediate bolts 46 may be adjusted to vary the spacing between end caps 48.

Vibrator motors 34 are preferably installed by manually pushing the end caps 48 into the assembled position of FIG. 3, as shown in FIGS. 3 and 4, and by then tightening intermediate bolts 46 to securely clamp the motors 34 in place. Alternately, the intermediate bolts 46 may be adjusted first and the end caps 48 may then be forced into the assembled position of FIGS. 3 and 4.

It should be noted in FIGS. 1 and 3 that the clamp arms 40, 42 are long enough to hold the vibrator motors 34 in a position offset below the bottom of springs 26. This is an important feature of the invention, since interference between springs 26 and vibrator motors 34 would prevent the end caps 48 from fully engaging the flange portion 30 of end rail 14. Therefore, when the vibrator motors 34 are in the mounted position shown in FIG. 1, the uppermost surface of motor housing 38 is at least below the top of the flange portion 32 of end rail 14.

FIGS. 2 and 5 show how vibrator motors 34 can be readily mounted on the side rails 52 of that type of bed which has a wooden headboard 54 and a wooden footboard 56. This type of bed has side rails 52 which are made of steel and which have ends attached to headboard 54 and footboard 56 by conventional means not shown.

Side rails 52 are L-shaped in cross-section and have upwardly-extending flange portions 58 (FIG. 5) and inwardly-extending flange portions 60. Slats 62 are supported by the flange portions 60 and in turn support a set of springs, such as the box spring 64, and a mattress 66. The clamp arms 40, 42 of vibrator motors 34 are clamped to the flange portions 60 of side rails 52 and project horizontally inwardly to hold the motors 34 in a position offset below the box spring 64. As is clear from FIG. 5, the attachment arms are accommodated below the box spring 64 in the space 70 provided by the thickness of the bed slats 62, the motor being offset below the frame in a non-interfering position.

Various changes may be made without departing from the spirit of the invention, and all of such changes are contemplated as may come within the scope of the claims.

What I claim is:

1. The combination comprising a bed structure including a frame having rail portions, a set of springs supported by said frame, at least one vibrator motor, means attaching said vibrator motor to a rail portion, said means comprising clamp arms projecting from said vibrator motor and having ends clampingly engaged with said rail portion, said arms being so disposed on said vibrator motor that the motor is supported in a position offset downwardly from said set of springs to prevent interference therewith, there being a bracket rigidly attached to one side of said vibrator motor and there being a pair of clamp arms attached to each end of said bracket by bolts, and a spacer sleeve around one bolt at each end of said bracket for spacing the clamp arms apart by a gap approximately equal to the thickness of the material of the rail portion to which the clamp arms are attached, said bracket being elongated at opposite ends beyond said vibrator motor to provide access to said bolts.

2. The combination defined in claim 1 wherein the bolts which pass through said spacer sleeves are located at the inner end of their respective pair of clamp arms, and further comprising another bolt passing through an intermediate portion of each pair of clamp arms for adjusting the gap.

* * * * *